United States Patent
Lewicke (10) Patent No.: US 7,438,687 B2
(45) Date of Patent: Oct. 21, 2008

(54) PATIENT MONITORING SYSTEM WITH BLOOD PRESSURE MEASUREMENT CAPACITY

(75) Inventor: John Lewicke, Mason, NH (US)

(73) Assignee: Nova Technology Corporation

( * ) Notice: Subject to any disclaimer, the term of this patent is extended or adjusted under 35 U.S.C. 154(b) by 227 days.

(21) Appl. No.: 11/161,698

(22) Filed: Aug. 12, 2005

(65) Prior Publication Data

US 2006/0036185 A1 Feb. 16, 2006

Related U.S. Application Data (60) Provisional application No. 60/601,423, filed on Aug. 14, 2004.

(51) Int. Cl.
*A61B 5/02* (2006.01)
(52) U.S. Cl. ....................... 600/485; 600/500
(58) Field of Classification Search .............. 600/481, 600/483–486, 488, 490–504
See application file for complete search history.

(56) References Cited

U.S. PATENT DOCUMENTS

| | | | |
|---|---|---|---|
| 3,742,937 A | 7/1973 | Manuel et al. | 128/2.05 |
| 3,905,354 A * | 9/1975 | Lichowsky | 600/494 |
| 4,776,339 A * | 10/1988 | Schreiber | 600/324 |
| 4,780,824 A * | 10/1988 | Niwa et al. | 600/513 |
| 4,924,871 A | 5/1990 | Honeyager | 128/672 |
| 4,987,900 A | 1/1991 | Eckerle et al. | 128/672 |
| 5,309,908 A * | 5/1994 | Friedman et al. | 600/322 |
| 5,363,855 A | 11/1994 | Drzewiecki et al. | 128/672 |
| 5,439,001 A | 8/1995 | Butterfield et al. | 128/672 |
| 5,511,553 A | 4/1996 | Segalowitz | |
| 5,515,858 A | 5/1996 | Myllymaki | |
| 5,722,414 A | 3/1998 | Archibald et al. | 128/672 |
| 5,833,602 A * | 11/1998 | Osemwota | 600/310 |
| 5,895,359 A * | 4/1999 | Peel, III | 600/494 |
| 5,931,790 A * | 8/1999 | Peel, III | 600/494 |
| 6,036,651 A * | 3/2000 | Inukai et al. | 600/485 |
| 6,186,954 B1* | 2/2001 | Narimatsu | 600/490 |
| 6,196,974 B1* | 3/2001 | Miwa | 600/490 |
| 6,198,394 B1 | 3/2001 | Jacobsen et al. | 340/573.1 |
| 6,428,481 B1* | 8/2002 | Inukai et al. | 600/485 |
| 6,454,708 B1 | 9/2002 | Ferguson et al. | 600/300 |
| 6,514,212 B1 | 2/2003 | Ide et al. | 600/490 |
| 6,733,447 B2* | 5/2004 | Lai et al. | 600/300 |
| 6,733,461 B2 | 5/2004 | Bratteli | 600/490 |
| 6,897,788 B2 | 5/2005 | Khair et al. | 340/870.16 |
| 2001/0044732 A1 | 11/2001 | Maus et al. | 705/3 |
| 2002/0120201 A1* | 8/2002 | Chio et al. | 600/490 |
| 2003/0004403 A1 | 1/2003 | Drinan et al. | 600/301 |
| 2003/0229276 A1 | 12/2003 | Sarussi et al. | |
| 2003/0236452 A1 | 12/2003 | Melker et al. | |
| 2004/0078227 A1 | 4/2004 | Morris | 705/2 |
| 2004/0147818 A1 | 7/2004 | Levy et al. | 600/300 |
| 2004/0167414 A1 | 8/2004 | Tanabe et al. | 600/500 |

* cited by examiner

*Primary Examiner*—Charles A. Marmor, II
*Assistant Examiner*—Navin Natnithithadha
(74) *Attorney, Agent, or Firm*—George A. Herbster (57) ABSTRACT

A patient monitoring system including a sensing-recording device that attaches to a patient and a probe utilized by attending personnel at a trauma site. After an initial interaction between the probe and the sensing-recording device, the sensing-recording device samples one or more physiological parameters and stores time stamped readings in a first memory. The probe is adapted to take other measurements including pulse data, download the data from the first memory of the sensing-recording device, manipulate the collective data and return data to a second memory in the sensing-recording device. The probe is also adapted to combine data from the sensing-recording device and its pulse data to provide a blood pressure measurement.

8 Claims, 11 Drawing Sheets

PATIENT MONITORING SYSTEM WITH BLOOD PRESSURE MEASUREMENT CAPACITY

FIELD OF THE INVENTION

This invention generally relates to monitoring physiological parameters of a patient and more specifically to the monitoring of such parameters in patients who are geographically remote from a medical facility.

DESCRIPTION OF RELATED ART

Monitoring of a patient's physiological parameters in a medical environment is an important element of patient diagnosis and treatment. Within a modern medical facility, such as a hospital, such monitoring is relatively easy to perform. The environment is controlled. The staff, including physicians, nurses, physician assistants and technicians, is qualified. Such facilities have equipment resources for enabling the monitoring of one or more patients for a variety of physiological parameters.

Unfortunately the advantages of a hospital environment with its resources and personnel do not exist at many trauma sites, such as those at accident scenes or at battlefield sites. First responders to an accident scene generally include an emergency medical technician (EMT). The EMT assesses the patient and, in conjunction with advice from medical personnel established by radio contact, initiates treatment. Typically the EMT stays with the patient during transport to a medical facility. The EMT can transfer his or her observations to personnel at the facility by interview and/or by written record.

An entirely different situation exists on a battlefield. On a battlefield a medic is attached to a particular unit. The medic treats a patient. When the medic completes treatment at the battlefield site, the patient is transported to another facility. However, the medic stays behind to attend to other patients. The medic's initial treatment protocol will be based on certain readings taken at the site. Then there are procedures for identifying the actions that were taken at the site. For example, if a sedative is administered, the medic may pin the syringe to the patient. Typically no interview occurs between the personnel at the medical facility, such as a field hospital, and the attending medic. Moreover, typically no information is recorded about the patient during initial treatment and transport to the field hospital.

Recently proposals have been made for personal monitoring systems for use in a battlefield environment. U.S. Pat. No. 6,198,394 (2001) to Jacobsen et al. discloses one such system for remote monitoring of personnel. This system utilizes a harness with a number of sensors to be worn continuously by a soldier. The sensors monitor a number of parameters including physiological variables. The harness carries a transmitting unit for transferring data to a central site.

U.S. Pat. No. 6,454,708 (2002) to Ferguson et al. discloses a portable remote patient tele-monitoring system using a memory card or a smart card. This system includes a multi-parameter sensor array applied to a patient's chest by means of a sensor band. The smart card or memory card stores measured data. Alternatively, a data logger carried by the patient receives the data. A base station receives the recorded information and transmits it to a remote monitoring site over a telecommunications link. The sensor band is disposable and has a limited life. For long-term monitoring, sensor bands may be replaced periodically.

U.S. patent Publication No. 2004/0147818 (2004) to Levy et al. discloses a portable system for monitoring and processing patient parameters in multiple operational modes. Specifically a data acquisition processor receives data from sensors on a patient and processes that data. The processed data is communicated to a docking station with a portable monitoring unit in one operational mode or to a network access point in a wireless network in another operational mode.

As will be apparent, each of these proposals requires the use of bulky equipment. The Jacobsen et al. patent requires a soldier to wear a harness to be worn at all times. First, such a requirement requires the soldier to carry extra weight and to take precautions to avoid damaging the equipment during normal use. It is not likely that such a harness would be an acceptable alternative for application to a trauma patient on a battlefield or at another trauma site. Such apparatus is bulky, so it would be difficult to inventory such harnesses for multiple patients. In addition, medical personnel would have the additional burden of placing the harness on a trauma patient under adverse circumstances.

Each of these systems depends upon the availability of sophisticated communications links, such as those available in a hospital environment. They are not always available at a trauma site or on the battlefield. The use of smart cards or memory cards as suggested in the Ferguson et al. patent present problems because such devices are prone to being lost at a trauma site or during patient transport to a hospital or other central site. Further, only the data measured at the trauma site is recorded.

Oftentimes it is desirable for a medic to obtain a patient's blood pressure at the trauma site. In accordance with a popular method, a medic inflates a blood pressure cuff and then slowly deflates the cuff while monitoring the radial artery with a stethoscope to obtain the systolic and diastolic pressure readings. These devices are bulky for field use. Moreover, they do not record data. Consequently, the medic must record the blood pressure manually, typically by preparing a written record.

Other approaches have been proposed for providing various functions related to monitoring pulse waveforms and the like. For example, U.S. Pat. No. 3,742,937 (1973) to Manuel et al. discloses a cardiac monitor for generating an alarm if a patient's heart rate exceeds a threshold. The monitor includes a pressure sensitive diaphragm for sensing the pulse wave transmitted from the heart. A mechanico-electrical transducer, in the form of a strain gauge or capacitive element converts the pulse into a digital signal.

U.S. Pat. No. 5,722,414 (1998) to Archibald et al. discloses a blood pressure monitoring system including a transducer, a side wall, a flexible diaphragm and a fluid coupling medium. This sensor is adapted to be strapped to the wrist and includes means, including an electric motor for properly positioning and maintaining pressure during the measurement.

U.S. Pat. No. 6,514,212 (2003) to Ide et al. discloses a hemadynamometer with an air bag that is wrapped about the wrist for obtaining oppression or ischemia of the radial artery. A pneumatic pump pressurizes the air bag until ischemia is realized. A constant exhaust valve then gradually exhausts the bag while a pressure sensor detects the pulse signals of the radial artery. These signals are converted to digital signals for analysis and for obtaining blood pressure.

U.S. patent Publication No. US 2004/0167414 (2004) to Tanabe et al. discloses pulse wave monitoring device for obtaining a physiological characteristic such as an arteriosclerosis index.

Each of these approaches also tends to be bulky and expensive. What is also needed is a patient monitoring system that is adapted for providing a blood pressure measurement at a trauma site. What is also needed is a patient monitoring system that enables a recorded blood pressure at a trauma site to be electronically recorded for transport with the patient to a hospital or other medical facility. What is also needed is a patient monitoring system in which the components required for obtaining blood pressure can be combined with components for providing other functions.

SUMMARY

Therefore it is an object of this invention to provide patient blood pressure measurement apparatus that is adapted for use in a variety of environments including battlefield environments.

Another object of this invention is to provide apparatus for measuring blood pressure upon the arrival of a first responder or medic at a site and recording that measurement for transport with the patient to a medical facility.

Yet another object of this invention is to provide patient monitoring apparatus that is easy to use and facilitates the measurement of blood pressure.

In accordance with one aspect of this invention, apparatus for recording a pulse waveform generated at a measurement site on a patient's body includes a rigid housing that can be brought into proximity to an artery at the measurement site. A pressure transducer mounts to one side of the housing for generating an electrical signal that is a function of pressure at an input to the pressure transducer. A passage is formed through the housing from the input of the pressure transducer to communicate with the interior of bladder mounted to the other side of the housing. The bladder forms a sealed, fluid-filled cavity at the passage. Consequently when the bladder is brought into contact with skin at the measurement site, the pressure transducer produces a representation of a wave-form signal including pressure changes due to changes in the blood pressure in the artery.

In accordance with another aspect of this invention a system for obtaining a measurement of a patient's blood pressure includes a sensing-recording device and a probe. The sensing-recording device attaches to the patient and includes a memory, at least one sensor for measuring a physiological parameter and a memory for storing time-stamped samples of the physiological parameter in said memory. The probe is adapted for being applied with an application pressure to a measurement site remote from the site of said sensing-recording device. The probe generates a signal representing a pulse wave form at the measurement site for storage in a probe memory as time-stamped samples of the signal. The probe generates a representation of the patient's blood pressure based upon the retrieved time-stamped samples from said memory in said sensing-recording device in the probe memory.

In accordance with still another aspect of this invention a sensing-recording device that provides to an output device a history of a medical parameter of a patient includes a housing, a power supply in the housing and circuitry for storing in a memory data that represents the medical parameter. A normally open switch includes a locking structure that is operable when the switch is closed energizing the circuitry thereby to block any attempt to disconnect the power supply from the circuitry.

BRIEF DESCRIPTION OF THE DRAWINGS

The various objects, advantages and novel features of this invention will be more fully apparent from a reading of the following detailed description in conjunction with the accompanying drawings in which like reference numerals refer to like parts, and in which.

DESCRIPTION OF ILLUSTRATIVE EMBODIMENTS

Figure 1:
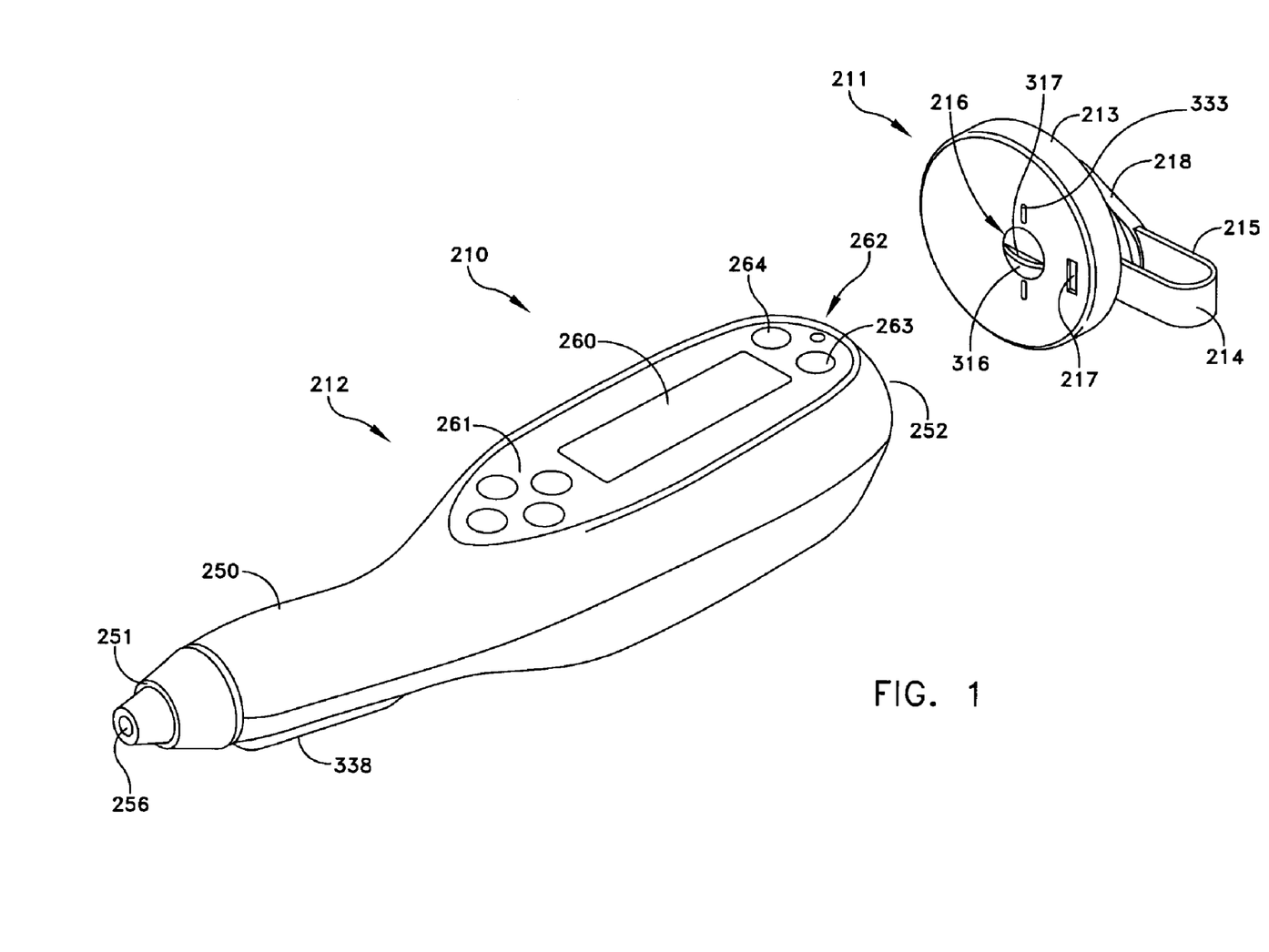
FIG. 1 depicts monitoring apparatus in accordance with this invention.
Figure 2:
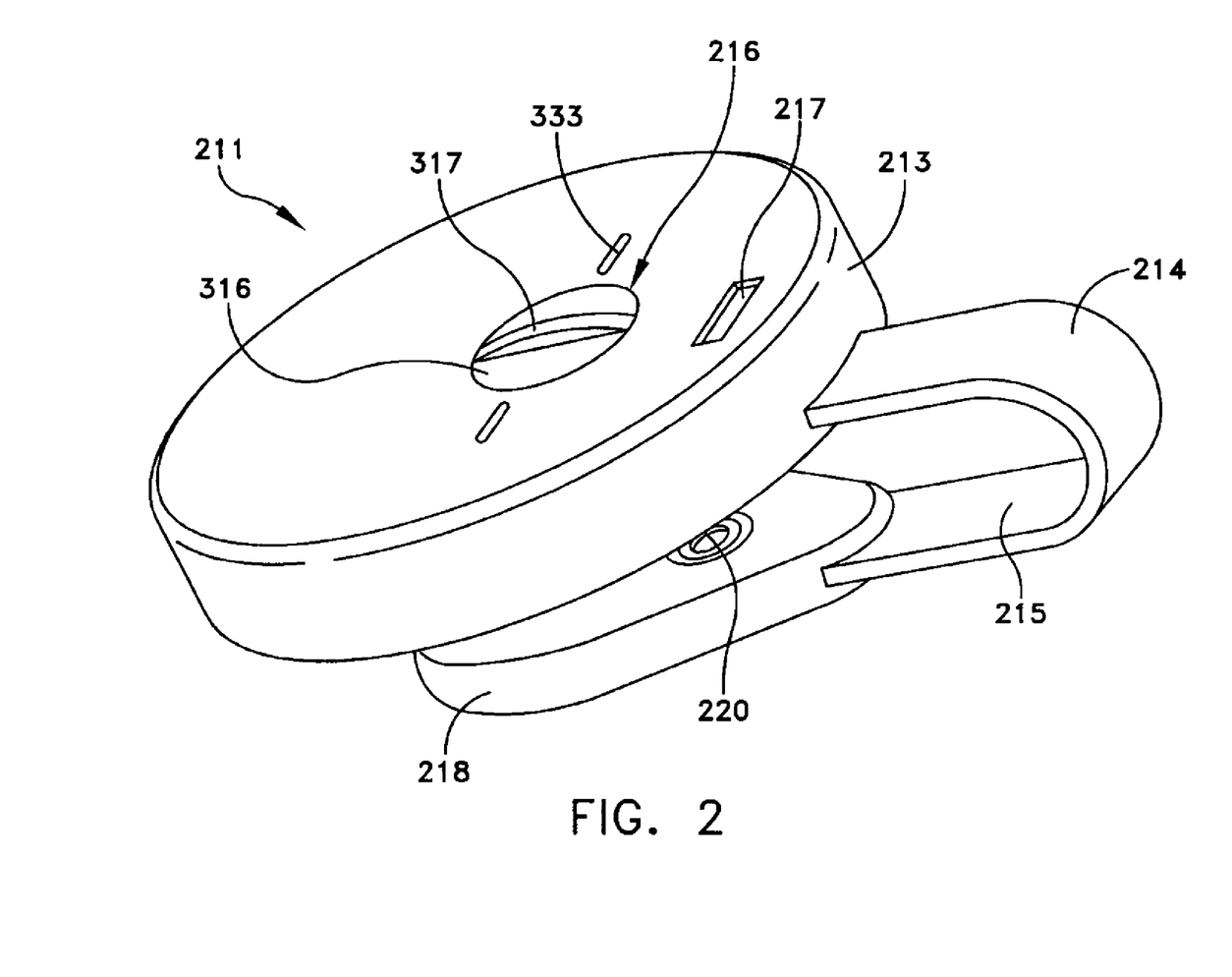
FIG. 2 is a different perspective view of a sensing-recording device shown in FIG. 1.

In FIG. 1 patient monitoring apparatus 210 includes a sensor button 211 that includes the capability of sensing and recording data related to a medical parameter, hereinafter a "sensing-recording device" and a probe 212. A medic can carry multiple sensing-recording devices and attach one sensing-recording device 211 to each patient. In the following discussion the term "medic" normally identifies military personnel; however, in conjunction with this invention the term includes both military personnel and civilian personnel, such as EMTs. Each medic will also have a single probe 212. An individual probe 212 may be used in conjunction with multiple sensing-recording devices, such as the sensing-recording device 211, for multiple patients.

Sensing-Recording device 211

As particularly shown in FIGS. 1 through 4, the sensing-recording device 211 includes a base unit or housing 213, a clip having a transverse portion 214 and a clip arm 215 spaced from and essentially parallel to the housing 213. The housing 213 carries an on/off switch 216 and a portion of a communications link in the form of an IrDA (Infrared Data Association) transceiver located behind window 217 in FIG. 1. The clip arm 215 and housing 213 provide a means for attaching the sensing-recording device 211 to the patient. For purposes described later, the free end of the clip arm 215 may include a tear-drop portion 218 or other like element partially for patient comfort.

Figure 5:
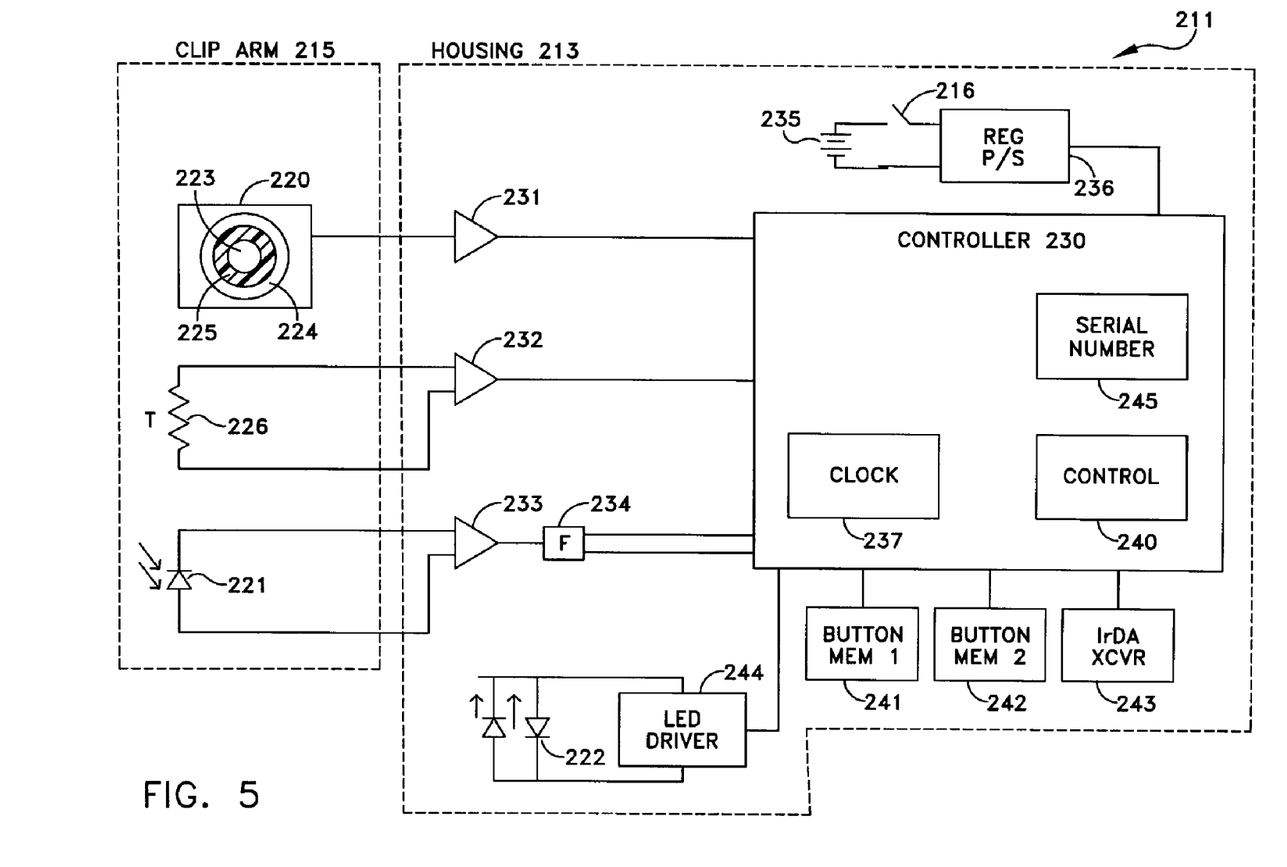
FIG. 5 is a block diagram of the circuitry associated with the sensing-recording device shown in FIGS. 1 through 4.

Both the housing 213 and arm 215 include sensing elements. In the embodiment shown in FIG. 2 the clip arm 215 carries a sensor, such as represented by a dermal phase meter (DPM) electrode assembly 220. The clip arm may also include a temperature sensor 226 and photocell 221 as shown in FIG. 5. These sensors connect through conductors embedded in the clip arm 215 and link 214 to circuitry in the housing 213. The housing 213 may include other elements such as light emitting diodes (LED) 222 (shown in FIG. 5) for generating light in the red and infrared bandwidths for being sensed by the photocell 221 for pulse oximetry as known in the art. When a sensing-recording device includes optical devices in the clip arm 215, the tear-drop portion 218 serves to reduce ambient energy from reaching these sensors. It will become apparent that other sensors could be substituted for each or all of these specific sensors or added thereto.

In use a medic will, upon arrival at a patient, attach one sensing-recording device 211 to that patient. For example the sensing-recording device 211 could be attached by sliding the clip arm 215 into the patient's mouth and positioning the housing 213 on the patient's cheek.

FIG. 5 is a block diagram of the circuitry of the sensing-recording device 211. As shown, the clip arm 215 includes the DPM electrode assembly 220 with an inner electrode 223, an outer annular electrode 224 and intermediate annular insulator 225.

In this embodiment the temperature sensing element 226 is also included in the clip arm 215. It is shown separately in FIG. 5, but can be incorporated as part of the DPM electrode assembly 220. FIG. 5 also depicts the photocell 221.

Each of these sensors produces a signal that is transferred to a controller 230 located in the housing 213. In this specific embodiment amplifiers 231 and 232 convey amplified analog signals representing skin impedance and temperature to the controller 230. An amplifier 233 and filter 234 provide signals to the controller 230 from the photocell 221 representing specific frequencies of the light emitted by the LEDs 222.

When the on/off switch 216 closes there is a connection between a battery 235 and a regulated power supply (REG P/S) 236 for energizing the controller 230 with an internal clock 237. A control 240 operates so the controller 230 interacts with memory. In this specific embodiment the memory is partitioned into BUTTON MEM 1 memory 241 and BUTTON MEM 2 memory 242. Other partitioning or even separate memories could also be used. As will become apparent, functionally the memory can be considered as having two partitions. The controller 230 also interacts with the IrDA transceiver 243 that would be located behind the window 217 in FIG. 1.

Figure 3:
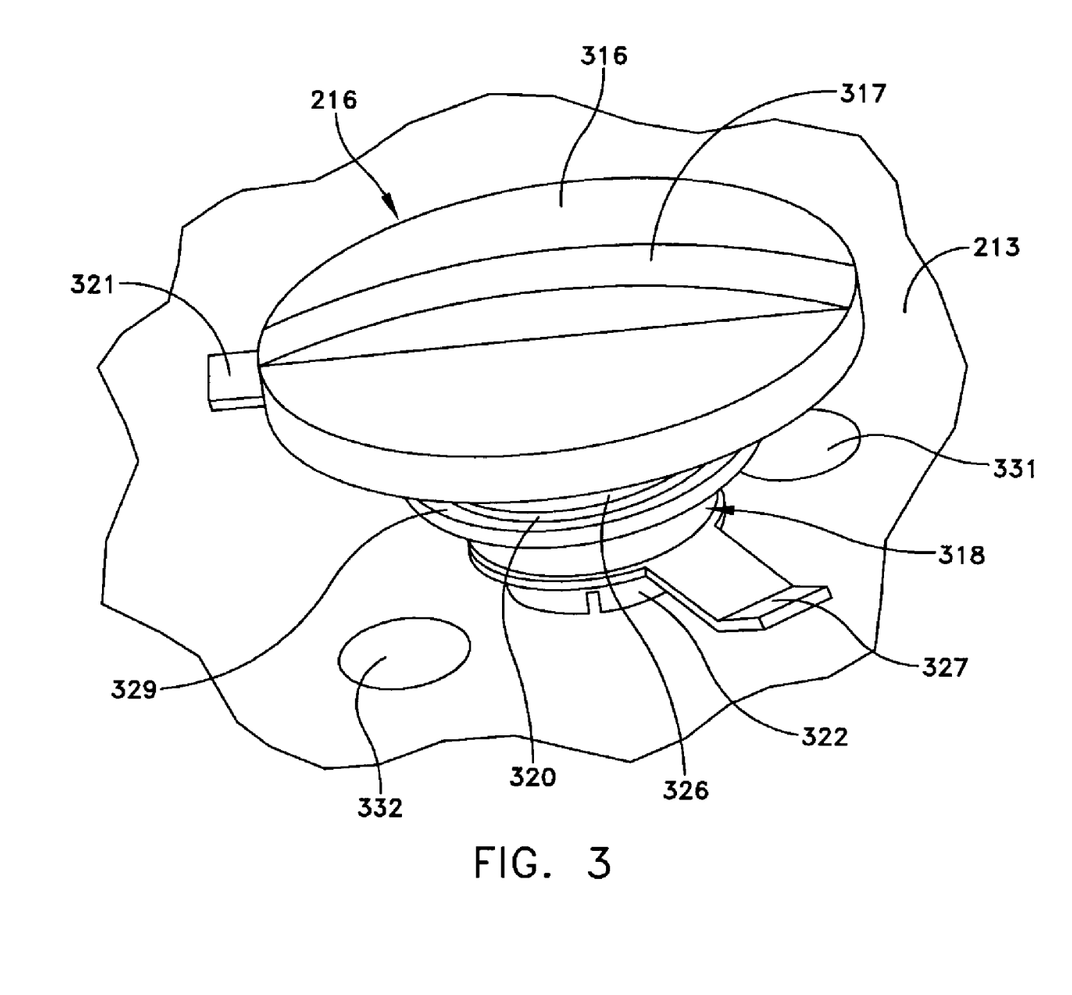
FIGS. 3 and 4 are two views of the interior of the sensing-recording device shown in FIG. 2.
Figure 4:
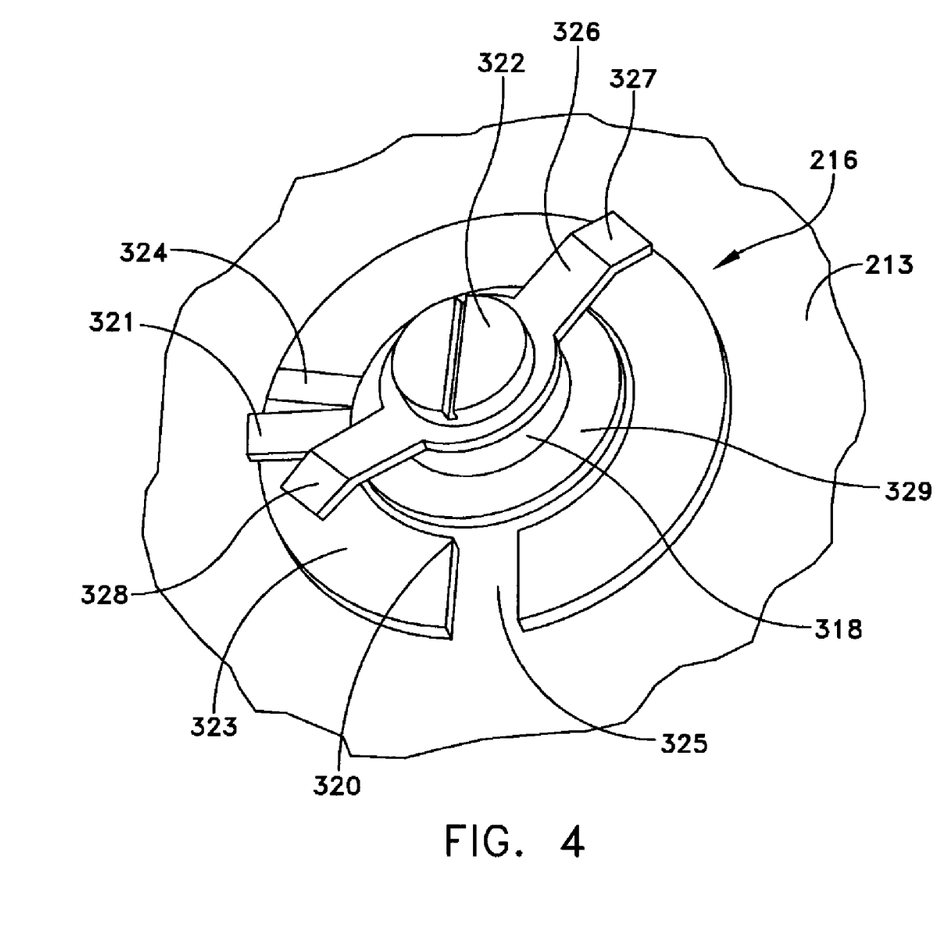

FIGS. 3 and 4 depict a view of a disposable sensing recording device 211 and particularly the structure of an ON/OFF switch 216 that is particularly adapted for use with this device. Switch 216 is designed to be moved from an OFF or open position that corresponds to its storage position to an ON position thereby energizing the components within the sensing-recording device 211. Once the sensing-recording device 211 is energized, it is imperative that it continue to be energized until the patient arrives at a medical facility and all the data is downloaded from the sensing-recording device 211.

As shown in FIGS. 3 and 4, the ON/OFF switch 216 includes a cover 316 with a diametrically extending rib 317 that facilitates manual rotation of the cover 316 and its underlying components. The cover 316 attaches to a shaft 318 mounted for a rotation in the housing 213 between a manually-open position and a closed position. Referring particularly to FIG. 4, the shaft 318 carries a first spring 320 with a single radial arm 321 keyed to the shaft 318. A machine screw 322 attaches the foregoing and other components to the shaft 318. In an OFF, or manually-open position the arm 321 lies on an arcuate segment 323 abutting a post 324. There is a gap 325 in the arcuate segment 323 that defines an ON or closed position. Thus when the cover 316 is rotated, it rotates from the OFF position shown in FIG. 4 to the ON position, the radial arm 321 locks into the gap 325 and prevents any further rotation of the cover 316.

As the cover rotates from the OFF position to the ON position, a spring contact 326 keyed to the shaft 318 also rotates. It has two diametrically opposed radially extending electronically interconnected arms 327 and 328. In an OFF position the arms 327 and 328 contact insulating material. When the switch reaches the ON position the spring contacts 327 and 328 overlie conductive pads 331 and 332, respectively. As shown in FIG. 1, rib 317 is at right angles to indicia 333 on the surface of the housing 213. When the cover 316 rotates to the ON position, the rib 317 aligns with the indicia 333 thereby to provide a positive indication that the sensor-recording device 211 has been energized. Moreover, as will be apparent, once the switch 216 is turned on, it can not be turned off. This assures that the sensing-recording device 211 remains active for the life of the batteries 235 in FIG. 5.

Thus after sensing-recording device 211 has been attached to a patient, the medic rotates the on/off switch 216 to energize the controller. As described in more detail later, communications are then established between the probe 212 and the sensing-recording device 211. When this occurs, a control 240 begins to sample the outputs of the various sensors from the clip arm 215 and activates an LED driver 244 to begin the measurement sampling sequence. The control 240 transfers each sample into the BUTTON MEM 1 memory 241. Typically the BUTTON MEM 1 memory 241 will have a capacity to store samples for 12 hours or so and may also act as a FIFO stack. In a preferred embodiment no sampled data is applied to the BUTTON MEM 2 memory 242.

In response to other communications the control 240 decodes information from an IrDA transceiver 243 for being loaded into BUTTON MEM 2 memory 242 and for transferring data from the BUTTON MEM 1 memory 241 to the probe 212. The controller 230 also includes circuitry (not shown, but known in the art) for converting signals from the various sensors in the clip arm 215 into digital formats for recording in the BUTTON MEM 1 memory 241. Each sample is time-stamped with information from the clock 237. As described later, the time in the clock 237 is established by communications between the probe 212 and the sensing-recording device 211.

The controller 230 also may include a storage register 245 for storing a permanent unique serial number. As described later, this serial number is useful in assuring that data about one patient is not inadvertently transferred to the sensing-recording device 211 for another patient.

Probe 212

Figure 6:
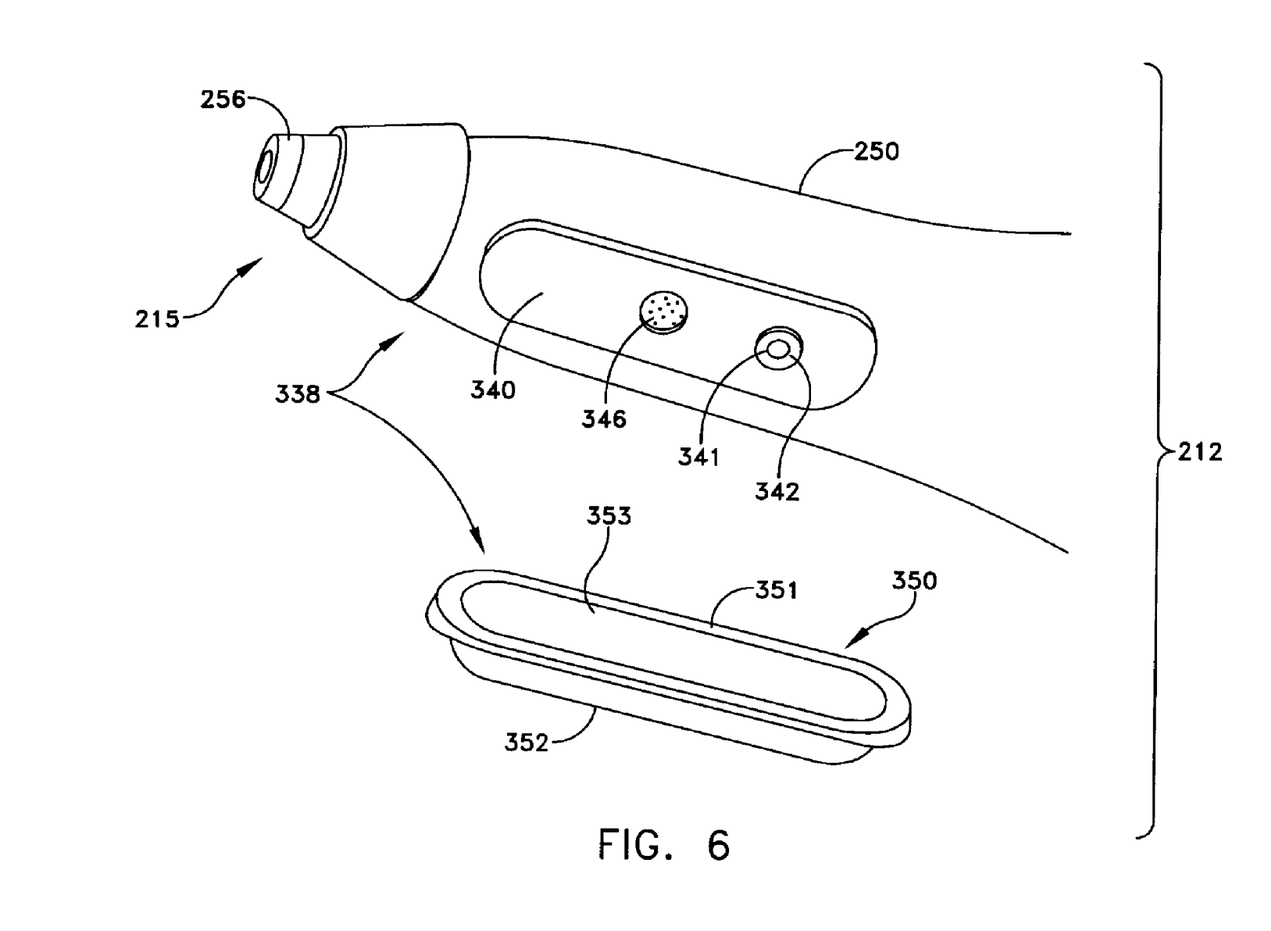
FIG. 6 is an exploded perspective view of a portion of the probe shown in FIG. 1.
Figure 7:
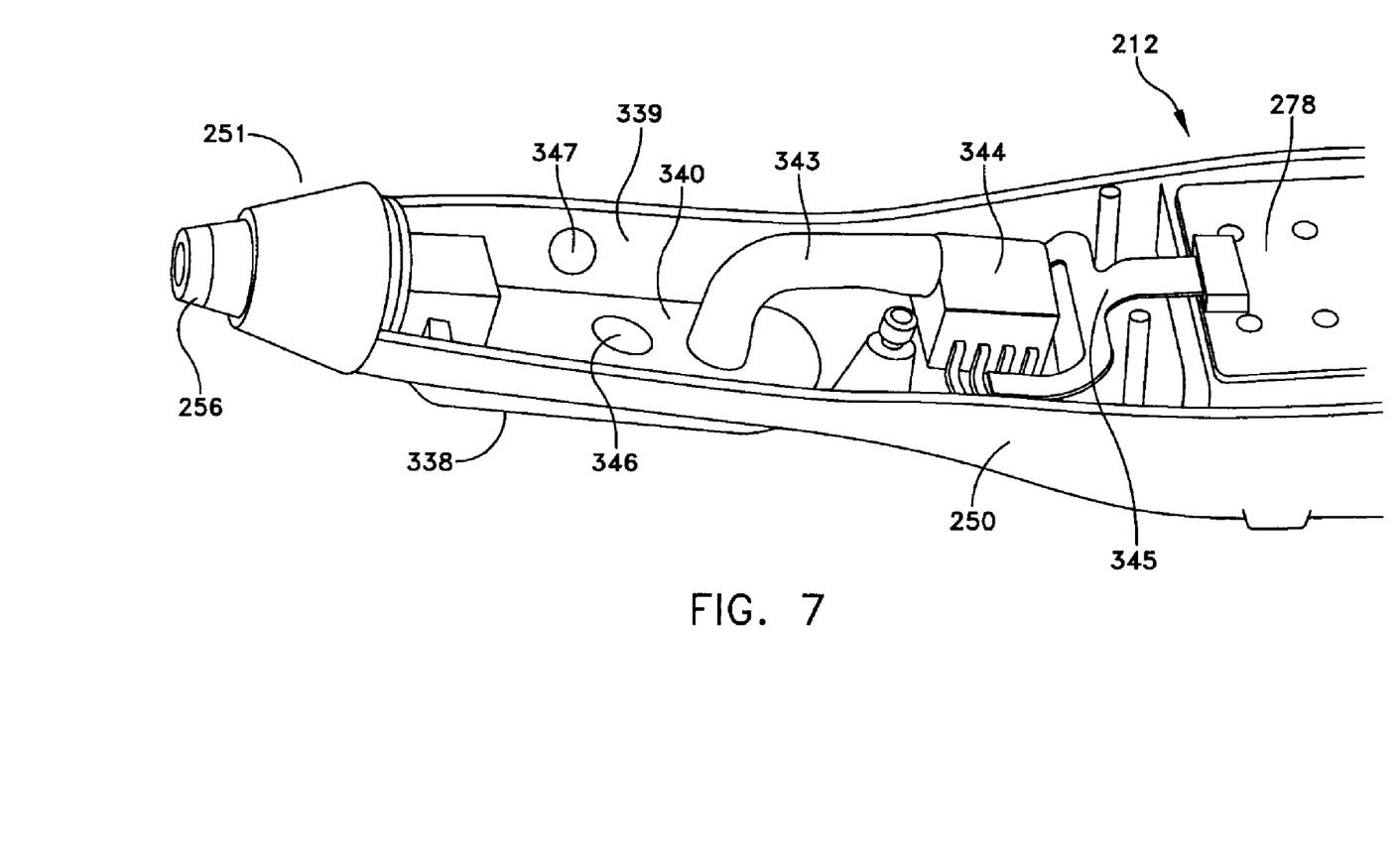
FIG. 7 is a view of the interior of the portion of the probe shown in FIGS. 1 and 6.

Now referring to FIGS. 1, 6 and 7, probe 212 has a housing 250 that extends between opposite end portions 251 and 252. The end portion 251 carries a DPM electrode assembly 256. This DPM electrode assembly 256 may also include a temperature sensor, not shown.

The housing 250 also carries a digital display 260 proximate the other end portion 252 as shown in FIG. 1. In this specific embodiment, a first keypad 261 has four scroll buttons for allowing the medic to move information on the display 260 transversely or parallel to the probe axis. Another keypad 262 may include an on/off button 263 and an "ENTER" button 264. Other structures may be substituted.

Referring to FIG. 1, the probe 212 includes an IrDA transceiver, not shown in FIG. 1, but located in the end of a housing 250 behind a window at the end portion 252.

FIGS. 1, 6 and 7 disclose a probe 212 that carries a bladder assembly 338 and forms a chamber 339 in which the various probe components are carried that can provide signals representing the pulse wave-form of the radial artery or of some other measurement site. As specifically shown in FIG. 6, the exterior surface of the housing 250 includes an integrally formed, raised platform 340. An insert 341 has an aperture 342 that provides a fluid passage. This insert terminates in a stub on the interior of the housing 250 which is not shown. Referring to FIG. 7, tubing 343 attaches to the stub and to a pressure transducer 344. FIG. 7 depicts a representation of a connector assembly 345 that interfaces the pressure transducer 344 to a probe controller 278.

FIGS. 6 and 7 also depict a controlled leak element 346 that extends through the platform 340. A controlled leak element, such as controlled leak element 346, is well known in the art as a means for slowly achieving equal pressure on both sides of the controlled leak element 346. In this particular embodiment a disk includes a plurality of chemically-milled apertures.

In addition the housing 347 as shown in FIG. 7 may include a second controlled leak element 346 that interfaces between the pressure on the chamber 339 and ambient atmosphere.

Referring again to FIG. 6, the bladder 338 is completed by means of a membrane 350 formed of a non-allergenic soft, compliant, thin, elastomer material, such as a silicone-based material. A peripheral flange 351 adheres to the housing 250 adjacent the periphery of the platform 340. A concave portion 352 integral with the flange 351 produces a closed end channel chamber 353 which has fluid communications with the pressure transducer through the aperture 342 and tubing 343 in FIG. 7.

When a medic wishes to take a measurement, the probe 212 is placed over a measurement site, such as the radial artery and a force is applied typically by squeezing the probe 212 against the patient's arm with the bladder 338 positioned over the measurement site. With appropriate pressure, pressure changes are conveyed through the thin material of the membrane 350, the fluid in the cavity 353 and then through the aperture 342 and tubing 343 to the input of the pressure transducer 344.

The value of the output signal 344 represents the instantaneous pressure within the bladder 338. This instantaneous pressure has two components. A first component is the pressure due to the force with which the probe is applied to the patient's arm. The second is due to the pressure within the artery being measured. The first component will vary slowly in comparison to the second component over time.

Figure 8:
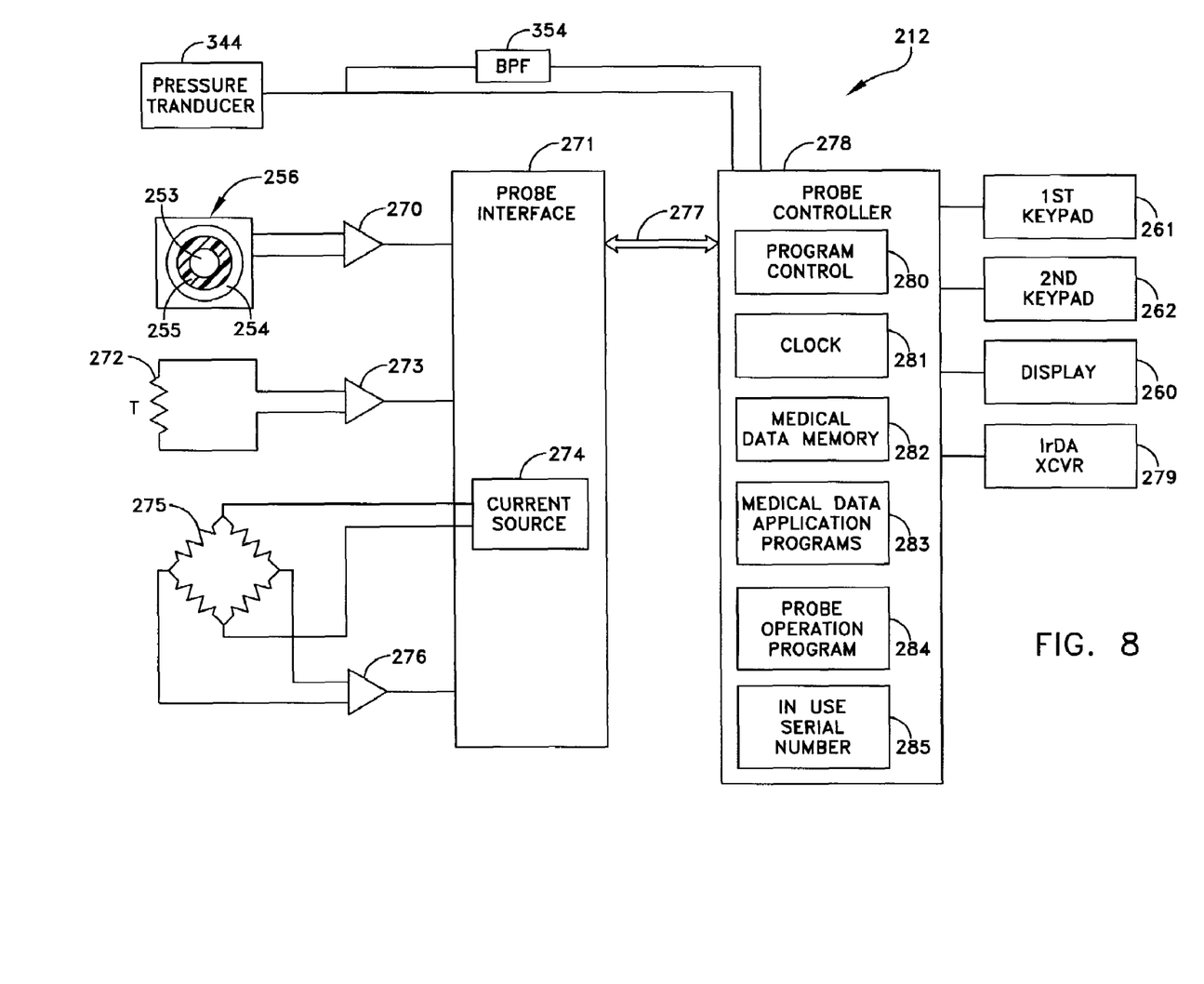
FIG. 8 is a block diagram of the electronic circuitry of the probe of FIGS. 1, 6 and 7.

FIG. 8 depicts one embodiment of control circuit for providing the various probe functions. An amplifier 270 provides signals from the DPM electrode assembly 256 to a probe interface 271. The probe interface 271 also interfaces signals from a temperature responsive element 272 provided by an amplifier 273 and includes a current source 274 for energizing a bridge 275 so an amplifier 276 produces a force measurement signal. The bridge 275 can be collocated with the temperature sensor 272 and DPM electrode assembly 256 as known in the art.

Basically the probe interface 271 converts signals from the various sensors into a digital format for transmission across a path 277 to a computer-driven probe controller 278. The probe controller 278 also interfaces with the first and second keypads 261 and 262, the display 260 and an IrDA transceiver 279 that is located behind a window at the end 252 of the probe 212.

The probe controller 278 includes a program controlled central processor represented as a program control 280. The probe controller 278 also includes a clock 281 that can be synchronized to any real time through interaction between the display 260 and the keypads 261 and 262. A medical data memory 282 stores any information provided by medical data application programs 283, such as an OMAS program for converting signals from the various sensors attached to the probe interface into an Oral Mucositis Assessment Scale (OMAS) value or, for implementing one embodiment of this invention, a blood pressure measurement program. The medical application programs 283 produce the data in the medical data memory 282 along with time stamps based upon information from the clock 281. All these operations occur in response to a probe operation program 284.

The probe controller 278 additionally includes an "in use" serial number register 285 for use as described hereinafter.

Still referring to FIG. 8 and as previously described the output signal from the pressure transducer 344 shown in FIGS. 7 and 8 represents the instantaneous total pressure applied at the input of a transducer 344. This output signal is defined as a raw data signal and it is conveyed to the probe controller 278. A band pass filter 354 also receives the raw data signal. The pass band for the filter 354 is in the range of 0.1 to 10 Hz to correspond to typical heart rates. The probe controller 278 also receives that signal as a filtered data signal.

Operation

Figure 9:
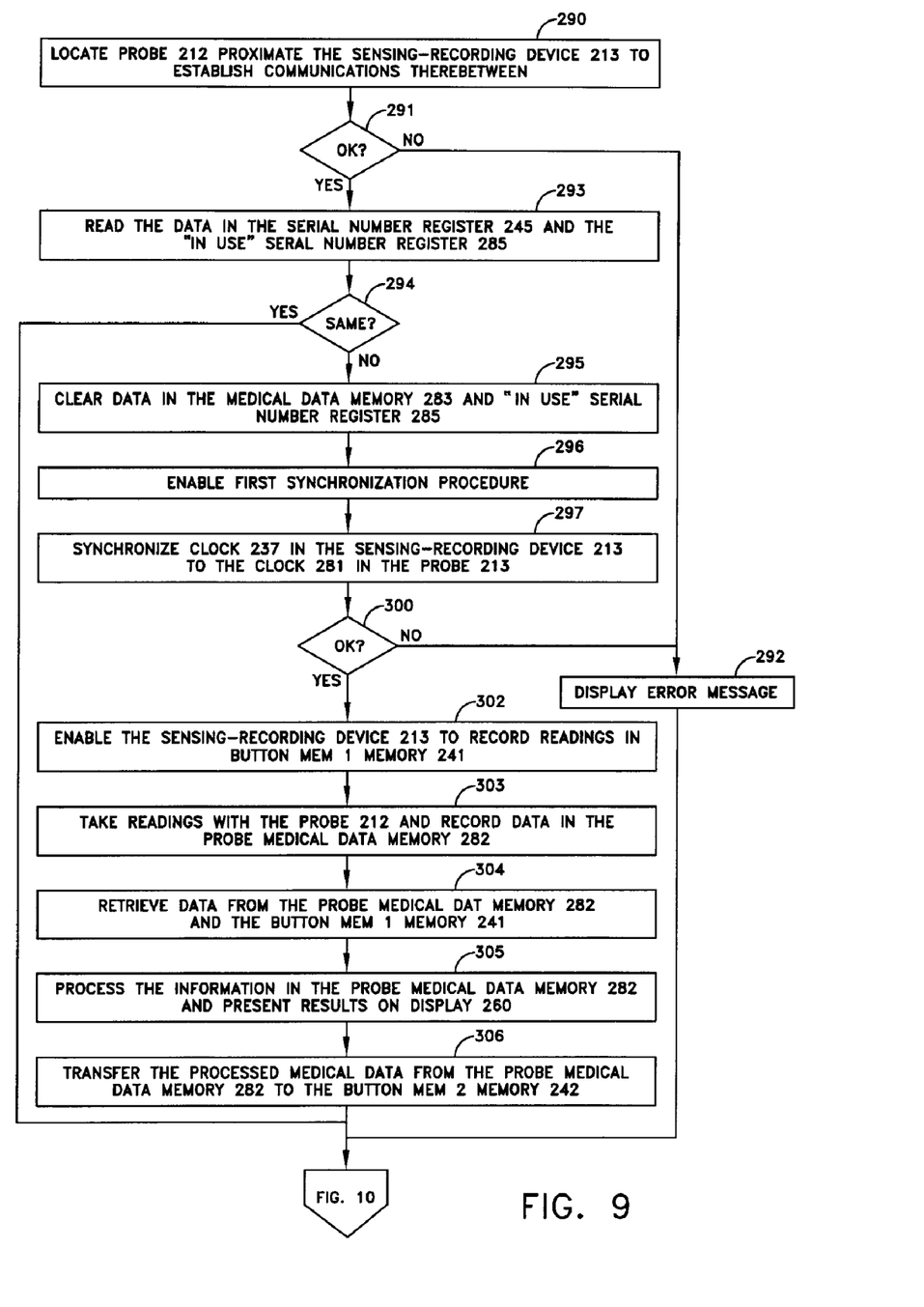
FIG. 9 is a flow diagram that depicts the operation of the probe and interaction with a sensing-recording device.
Figure 10:
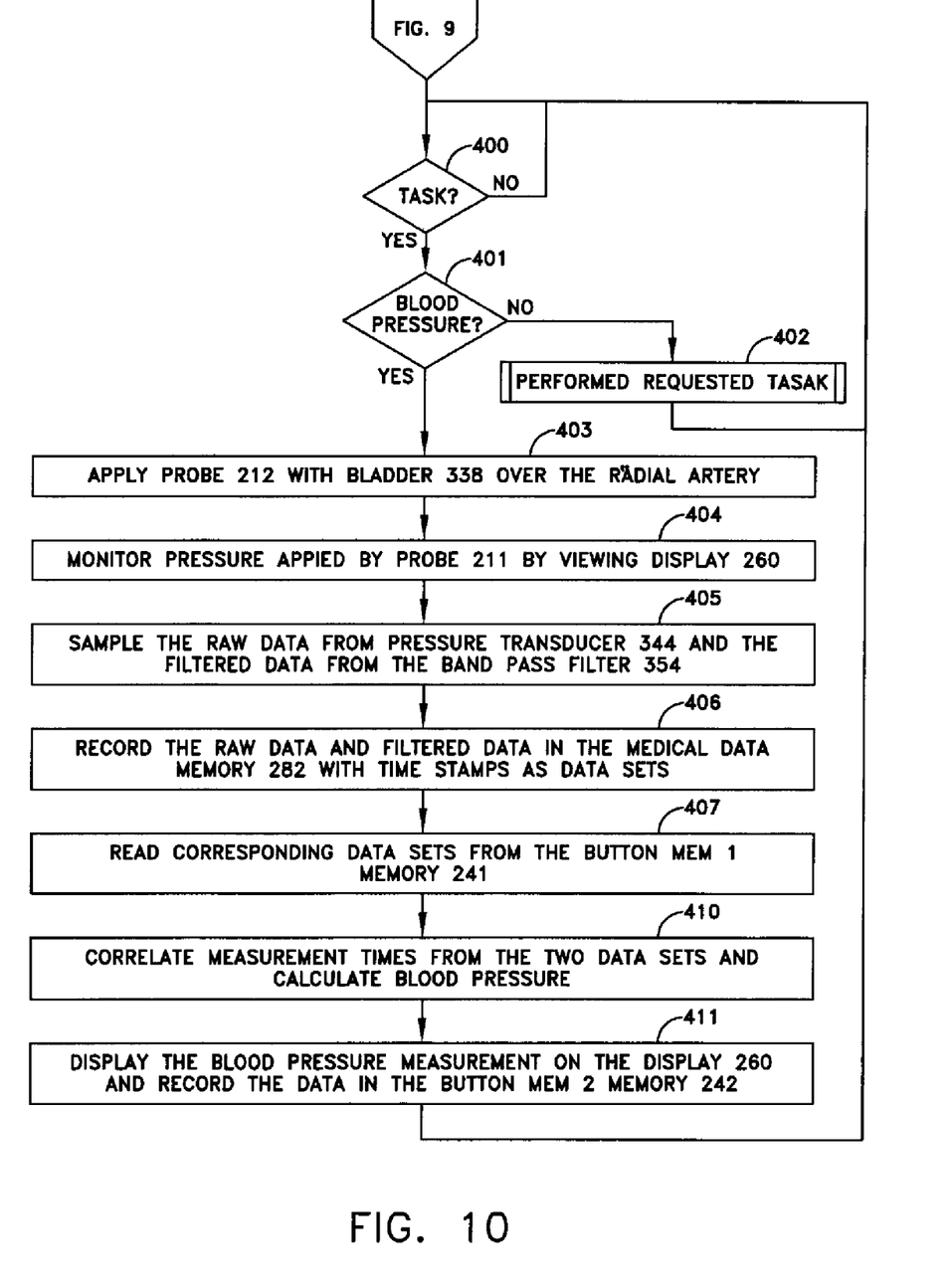
FIG. 10 is a flow diagram of one blood measurement method that can be undertaken using the probe and sensing-recording device of FIG. 1.

The probe operation program 284 as shown in FIGS. 9 and 10 defines a series of tasks including proposed actions to be displayed through instructions on the display 260 and reactions in response to data received either from the probe interface 271, the IrDA transceiver 279 or the keypads 261 and 262. A medic might be able to initiate the use of the probe 212 in a variety of ways. For example, the medic might manipulate the display using the keypad 261 in FIG. 1 until a "New Patient" procedure is displayed and then activate the ENTER key 263. FIG. 9 shows another approach in which the medic attaches a sensor-recording button 211 to a patient, turns the device 211 on and then brings the probe 212 into proximity to establish communications as indicated by step 290. If communications are not established after a predetermined period of time, step 291 transfers control to step 292 thereby to display an error message and to await a next action.

Assuming communications are established, control transfers to step 293 whereupon the probe reads the data in the serial number register 245 and the "in use" serial number register 285. If the medic is returning to the same patient, the serial numbers match. So, control passes from step 294 to FIG. 10. If the medic has not been working with a patient previously, the numbers are not the same and the patient is new. Step 294 diverts control to step 295 that clears the data in both the medical data memory 282 and "in use" serial number register 285.

Step 296 then enables a first synchronization procedure. Assuming that the medic has energized the sensing-recording device 211 by activating the on/off switch 216, step 297 synchronizes the clock 237 in the sensing-recording device 211 shown in FIG. 5 to the clock 281 in the probe controller of FIG. 8. Specifically, the clock 237 will have begun operation at some random time when the on/off switch has been activated. Step 297 allows the synchronization to occur and the clock 237 then to be updated. Typically the clock 237 will then run as accurately or nearly as accurately as the clock 281.

If the synchronization of step 297 can not be completed successfully, step 300 transfers control to step 292 to display an error message and potentially provide information with respect to recovering from the error.

Once the clock synchronization has occurred, the program operation control uses step 302 to communicate through the IrDA transceivers 243 and 279 in FIGS. 5 and 8 to enable the sensing-recording device 211 to record readings in the BUTTON MEM 1 memory 241. Step 303 represents a process during which a medic can use the probe 212 to take additional readings independently using one or more of the medical data application programs 283 with results being recorded in the probe medical data memory 282. These readings may also be under control of the program with appropriate displays specifying specific tasks to be taken.

When the medic has completed actions in step 303, step 304 initiates a process by which the medic retrieves information from the BUTTON MEM 1 memory 241 that contains the time stamped data relating to the monitoring operation by the sensing-recording device 211. When all the data has been retrieved, step 305 processes the information in the probe medical data memory 282, including the information from the BUTTON MEM 1 memory 241, to produce results as feedback to the medic according to medical data application programs 283. For example, one display might be a graphical representation of OMAS values over a period of time. During this interval, the sensing-recording device 211 continues to add data to the BUTTON MEM 1 memory 241.

When step 305 completes its operations, step 306 transfers selected data from the medical data memory 282 to the BUTTON MEM 2 memory 242. Thus the BUTTON MEM 2 memory 242 contains all the results of the readings taken by the medic at the battlefield site and the results of any data that was contained in the BUTTON MEM 1 memory 241 that was processed in step 305. When step 306 is completed, control transfers to step 400 in FIG. 10 to await the initiation of a new task.

FIG. 10 represents the process by which various tasks are initiated. As disclosed the probe controller 278 remains in a wait state until a task request is received in step 400. One of those tasks could be initiated by the medic through the keypads 261 and 262. When a task request is received, step 401 identifies the task. For tasks other than blood pressure, step 401 branches to step 402 for performing the requested task. When that is complete, control returns to step 400 to await the initiation of a next task.

When the medic wishes to take blood pressure, step 401 transfers to step 403 which represents the application of the probe 212 with the bladder 338 over the radial artery or other measurement site. As this occurs step 404 provides an indication on display of the value of the pressure.

More specifically, step 405 represents the sampling of the raw data from the pressure transducer 344 and the filtered data from the band pass filter 354. For each sample, the raw data and the filter data are stored in corresponding data sets with time stamps. In addition the processor may use a moving average over some time of the raw data to generate the signal representing the pressure being applied.

Figure 11:
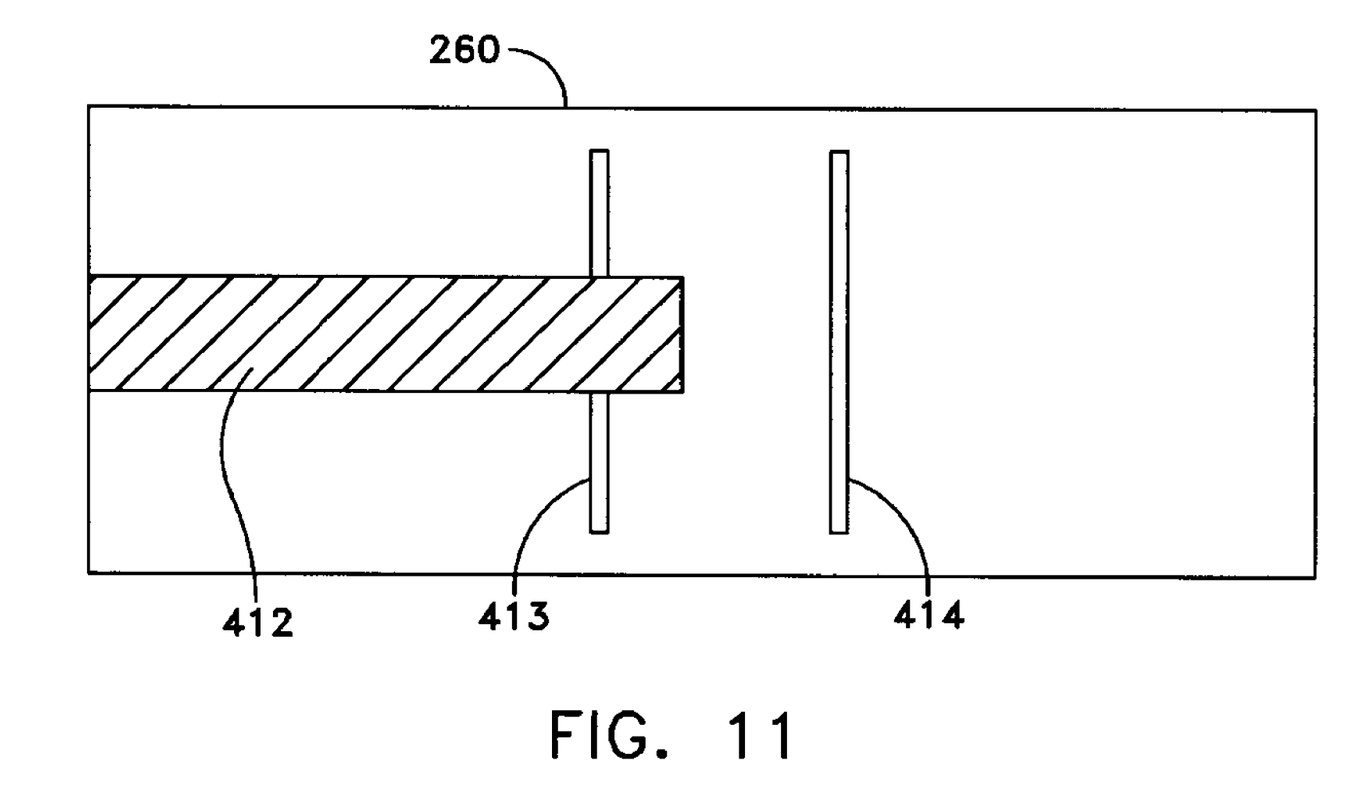
FIG. 11 depicts a graphical display obtained when making a blood pressure measurement.

As shown in FIG. 11 this average pressure value can be displayed as a bar graph 412 or by some other graphical representation. The display 260 will also provide two lines 413 and 414 bounding the acceptable range of force applied by the medic. Therefore the medic merely needs to observe this display to assure the optimal pressure is applied. The boundaries 413 and 414 may be fixed. Alternatively if a quality analysis is performed on the filtered data, the boundaries may be movable as a function of such analysis. This feedback is helpful in assuring appropriate pressures are applied by the medic.

After the information has been obtained and recorded in step 406, step 407 represents a process by which the corresponding data sets are read from the BUT 1 MEM memory 241, particularly the data representing the pulse oximetry obtained by the sensing-recording device 211. Step 410 then correlates the measurement times in the two data sets through a best fit or other analysis. The difference between the timing represents the times required for a particular pulse to travel from the heart to the patient's cheek and the heart to the radial artery. As known, this time of flight data is useful in deriving a blood pressure reading which then can be displayed by step 411. The data can also be recorded in the BUT 2 MEM memory 242. In this way the blood pressure is recorded and travels with the patient to the next medical facility. Alternatively the blood pressure measurement process of FIG. 10 could merely store the wave forms obtained during the blood measurement in the sensing-recording device 211.

Thus, when the patient is transported, the sensing-recording device 211 contains data in the BUTTON MEM 2 memory 242 that identifies his condition when the medic attended the patient. The BUTTON MEM 1 memory 241 contains the time stamped raw data that continues to be obtained from the various sensors in the sensing-recording device 211.

When the patient reaches a medical facility, it is a simple matter for a properly equipped data processing system, such as a laptop computer with an IrDA port, to communicate with the controller 230 in the sensing-recording device 211 and download all the data from both the BUTTON MEM 1 memory 241 and the BUTTON MEM 2 memory 242. This data can be further processed in accordance with various application programs to provide further diagnostic information. Unlike the prior art, however, this information provides a continuum of patient data from the time first synchronization procedure is initiated until the time the data is downloaded from the patient.

As will now be apparent, apparatus constructed in accordance with this invention and based upon the specific embodiment shown in FIGS. 1 through 10 provides patient monitoring apparatus that is adapted for use in a variety of environments including battlefield environments. This patient monitoring apparatus is easy to use and facilitates the measurement of diverse physiological parameters. Moreover, the apparatus enables the monitoring of these parameters from the arrival of a medic or a first responder at the patient to the arrival of the patient at a medical facility.

It will also be apparent that this invention has been described with respect to a specific embodiment with particular organization of components and controls. A number of variations can be made by those of ordinary skill in the art without departing from this invention. For example, the sensing-recording device 211 is shown with a structure particularly suitable for disposing the sensing-recording device housing 213 on a patient's cheek with the clip arm 215 within the mouth. Other form factors could be utilized that would adapt the function of the sensing-recording device 211 for attachment to other parts of the body, such as an earlobe, as might be dictated by a particular set of physiological parameters being measured. The probe 212 has been shown as a single device with particular form factor and layout of controls. Each of those could be modified to adapt the probe to different ergonomic or other conditions.

Similarly FIGS. 5 and 8 depict particular embodiments of the electronics carried within the sensing-recording device housing 213 and probe housing 250. Different sensors could be substituted for any of the specifically disclosed sensors. Different memory organizations could be utilized. Communications using mechanisms other than IrDA transceivers could be used. The organization of a control, such as the control 240 in FIG. 5 and the program control 280 in FIG. 8 could be changed. FIG. 8 depicts probe interface 271 and a probe controller 278. In other embodiments the functions of these two elements could be combined in a single unit. Consequently it is the intent to claim this invention to cover this particular embodiment and any equivalent embodiments that may be developed.

What is claimed is:

1. A system for obtaining a measurement of a patient's blood pressure comprising:
  A) sensing-recording means for attachment to the patient including a memory, sensing means for measuring a predetermined physiological parameter, and means for storing time-stamped samples of the predetermined physiological parameter in said memory as a first data set, and
  B) a probe for being applied with an application pressure to a measurement site remote from the site of said sensing-recording means, said probe including:
    i) means for generating a signal representing a pulse wave form at the measurement site,
    ii) a probe memory,
    iii) means for storing times-stamped samples of the signal in said probe memory as a second data set,
    iv) means for retrieving the time-stamped samples from said memory in said sensing-recording means,
    v) means for correlating the measurement times for the first and second data sets,
    vi) means for generating a representation of the patient's blood pressure based upon the information in said correlated, time-stamped data sets.

2. A system as recited in claim 1 wherein said probe comprises:
  i) rigid housing means for being brought into proximity to an artery at the measurement site,
  ii) pressure transducer means mounted to one side of said housing means for generating an electrical signal that is a function of pressure at an input thereto,
  iii) flexible membrane means mounted to the other side of said housing for forming a sealed, fluid-filled cavity about said passage means at said housing means, and
  iv) passage means formed through said housing means for connection to said pressure transducer means input whereby when said flexible membrane means is brought into contact with the skin at the measurement site, said pressure transducer means produces a representation of a wave-form signal corresponding to the pressure changes at the measurement site.

3. A system as recited in claim 2 wherein said flexible membrane means includes a thin, flexible elastomer formed into a closed-end channel and a peripheral flange attachment to said other side of said rigid housing means.

4. A system as recited in claim 3 wherein said rigid housing means forms a chamber for receiving said pressure transducer means, said apparatus including a controlled leak means for long-term pressure equalization between said cavity and said chamber.

5. A system as recited in claim 1 wherein said sensing means in said sensing-recording means includes means for measuring pulse oximetry whereby the first data set stored in said sensing-recording means memory represents blood oxygenation.

6. A system as recited in claim 5 wherein during a measurement said probe is applied to the measurement site with an application pressure and said pressure transducer means generates a composite signal representing the application pressure and the pressure at the measurement site, said probe including processing means for storing data representing the pulse wave form produced at the measurement site as the second data set.

7. A system as recited in claim 6 wherein said processing means includes band pass filter means for generating a filtered data signal in response to the composite signal whereby said processing means responds to both the composite and filtered data signals.

8. A system as recited in claim 7 wherein processing means includes means generating a graphical display of the application pressure in response to the composite data.

* * * * *